United States Patent [19]

Weiss

[11] Patent Number: 5,427,238
[45] Date of Patent: Jun. 27, 1995

[54] MAILER FOR SHARP MEDICAL WASTE

[75] Inventor: Mark E. Weiss, Denver, Colo.

[73] Assignee: OnGard Systems, Inc., Denver, Colo.

[21] Appl. No.: 80,206

[22] Filed: Jun. 23, 1993

[51] Int. Cl.⁶ .................. B65D 83/10; B65D 81/26
[52] U.S. Cl. ................................. 206/366; 206/204
[58] Field of Search ..................... 206/364–366, 206/370, 204; 220/403, 404, 408

[56] References Cited

U.S. PATENT DOCUMENTS

| | | | |
|---|---|---|---|
| 1,007,804 | 11/1911 | Schimmel | 206/365 X |
| 1,965,227 | 7/1934 | Fiero | 206/521 |
| 4,240,547 | 12/1980 | Taylor | |
| 4,315,592 | 2/1982 | Smith | |
| 4,454,944 | 6/1984 | Shillington et al. | |
| 4,494,652 | 1/1985 | Nelson et al. | |
| 4,520,926 | 6/1985 | Nelson | |
| 4,715,498 | 12/1987 | Hanifl | |
| 4,863,052 | 9/1989 | Lambert | |
| 4,869,366 | 9/1989 | Bruno | |
| 4,927,076 | 5/1990 | Simpson | |
| 4,931,139 | 6/1990 | Phillips | |
| 4,964,509 | 10/1990 | Insley et al. | 206/204 |
| 5,024,865 | 6/1991 | Insley | 206/204 X |
| 5,031,767 | 7/1991 | Bruno | 206/370 |
| 5,038,929 | 8/1991 | Kubofcik | 206/366 X |
| 5,040,678 | 8/1991 | Lenmark, Sr. et al. | 206/204 X |
| 5,067,223 | 11/1991 | Bruno | 206/366 X |
| 5,096,114 | 3/1992 | Higginbotham | 206/366 X |
| 5,160,021 | 11/1992 | Sibley et al. | 206/204 |
| 5,160,025 | 11/1992 | Greenwald | 206/204 X |
| 5,167,193 | 12/1992 | Withers et al. | 206/366 X |
| 5,291,997 | 3/1994 | He et al. | 206/370 |

Primary Examiner—Bryon P. Gehman
Attorney, Agent, or Firm—Larson and Taylor

[57] ABSTRACT

A mailer for sharp medical waste is comprised of a three-part system. A first part comprises a primary container for receiving the sharps and is puncture resistant and leak-proof. A second part comprises a secondary containment system in which the primary container is received and which prevents breakage of the primary container and also provides a water-tight seal. The third part comprises an outer shipping container which is constructed of a high-strength material and is similar in size and dimension to the secondary containment system, such that the latter fits securely therein. An absorbent material within the secondary containment system is capable of absorbing three times the liquid allowed within the primary container.

31 Claims, 5 Drawing Sheets

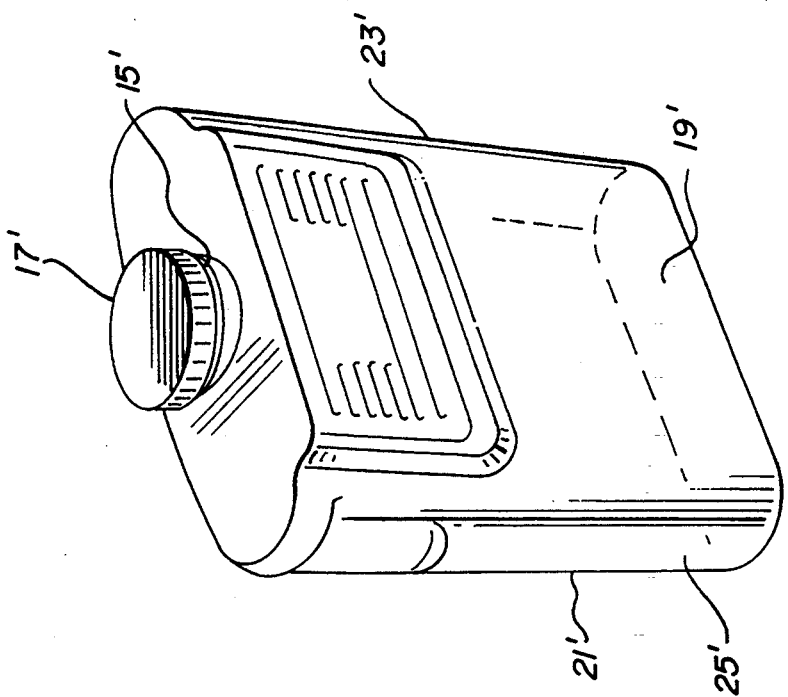
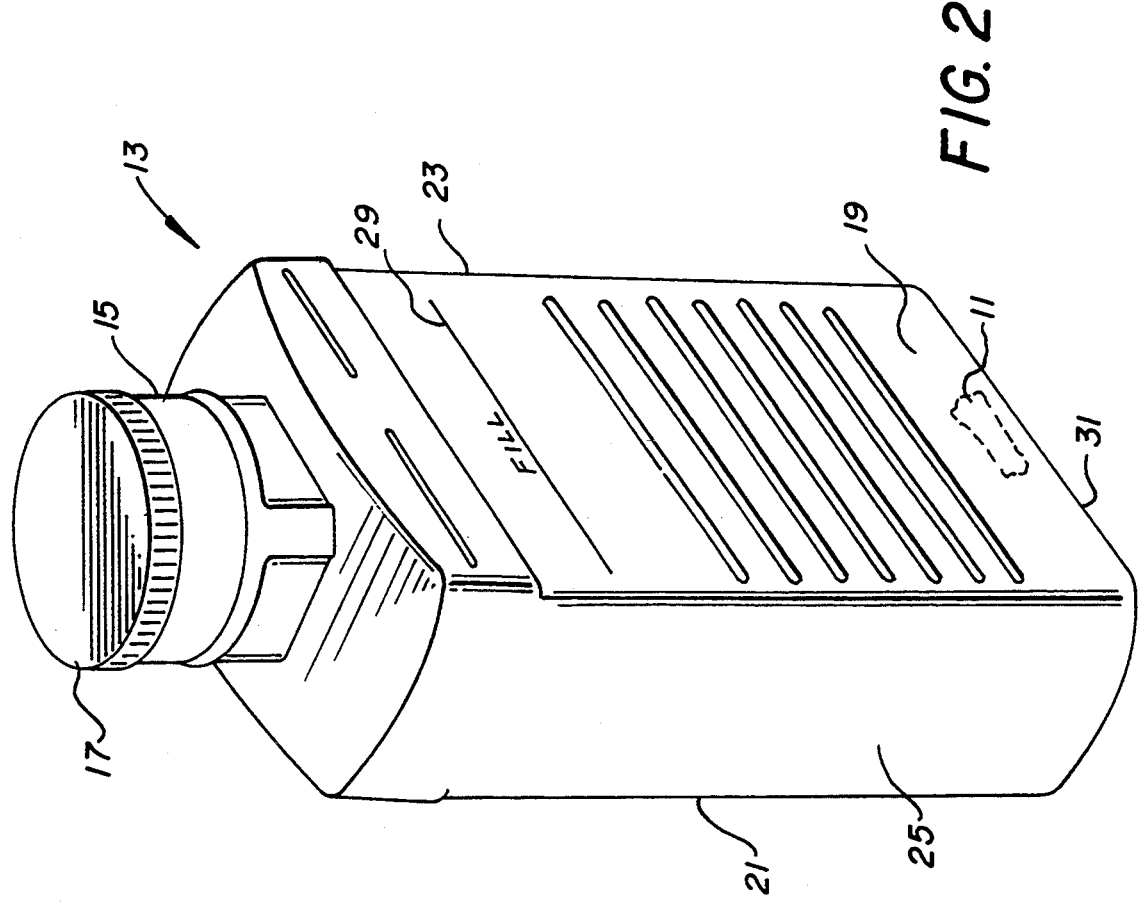

MAILER FOR SHARP MEDICAL WASTE

FIELD OF THE INVENTION

The present invention relates to a mailer for sharp medical waste and, more particularly, to a three-part packaging system which safely contains sharp medical waste from the time of contamination until disposal.

BACKGROUND OF THE INVENTION

Effective means of handling, storing and transporting contaminated sharp medical waste has become a problem of increasing concern. Sharp medical waste ("sharps") is generally defined as including any contaminated object that can penetrate the skin including, but not limited to needles, scalpels, broken glass, broken capillary tubes and exposed ends of dental wires. If not placed in an appropriate container after use, sharps clearly pose a hazard resulting from their potential to cut or puncture anyone handling them. Moreover, it is also now recognized that the spread of certain virulent diseases may result merely from contact with any type of medical waste.

Typically, sharps are deposited in a primary container, located in a doctor's office or laboratory, immediately after use. The contaminated sharps are stored in the primary container until their ultimate disposal. Containers for holding sharps must meet very specific requirements due to the stringent guidelines imposed by OSHA regarding their handling and storage. For example, the once common practices of recapping, breaking or cutting needles immediately after use to eliminate the sharp point is now prohibited by OSHA, with the exception of very limited circumstances, due to the potential for reuse or accidental puncture. Because the needles are not dismantled, they may also contain residual bodily fluids or medication which can splatter or emit noxious fumes. Consequently, the sharps container must be resistant to puncture by implements contained therein and also resistant to cracking, shattering or leakage. The sharps container should also have a central opening design which prevents removal of the sharps once they are inserted into the container.

Disposal methods for contaminated sharps include autoclaving followed by landfilling, high temperature incineration or other sanitary methods. While some hospitals may have appropriate disposal equipment on site, the majority of doctor's offices and other small health care facilities and laboratories are not equipped to handle the disposal of contaminated sharps. Consequently, it is necessary to send the contaminated sharps to another location for ultimate disposal. Many health care providers utilize the services of a waste hauling company to remove contaminated sharps. However, this type of service tends to be somewhat costly, as well as inconvenient because pick-ups of the contaminated sharps are only scheduled for specific days and times. A more cost effective and convenient option for disposal of sharps is to mail sharps containers to appropriate waste handling facilities.

There are, of course, several drawbacks associated with mailing sharps containers. For example, packages are often subjected to rough handling, temperature and climate changes, and other less-than-desirable conditions during transport through the postal system. Consequently, the mailer must also be constructed of a material which retains its integrity when exposed to temperature changes. The mailer should also protect the container from breakage and any possible content leakage.

Others have attempted to provide suitable containers for safe handling, storage and shipment of sharps. Typically, these containers comprise an inner, leak-resistant sharps container which is placed in a plastic bag for added leak protection. The container and plastic bag are then inserted into an outer corrugated fiberboard box containing a cellulose packing material, generally in the bottom of the box, which provides cushioning and also acts as an absorbent medium. A glue-on lid is often utilized to provide a leak-resistant seal on the sharps container. However, this type of system has not been found to be completely adequate for transport through the mail because the container is not adequately puncture resistant and is merely leak-resistant, not leakproof.

Another prior art container for handling contaminated sharps is shown in U.S. Pat. No. 5,031,767 to Bruno. This container includes a sharps container with a corrugated paperboard storage and transport housing, a substantially rigid fiberboard storage container slidably inserted within the housing for receiving and storing the implements, a plastic bag surrounding the storage container and entry formed on the container with a releasably insertable plug. A similar disposable container for handling biohazardous waste material is shown in U.S. Pat. No. 4,978,028 to George et al. This container comprises a substantially rectangular exterior box having an open top with a closure and an access hole for dropping waste material into the container, a polyethylene liner inserted in the exterior box, an inner box positioned at the base of the exterior box and an insert having an open top and bottom, the exterior box, inner box and insert being constructed of 200 pound C-Flute corrugated cardboard. However, neither the Bruno nor the George et al. containers provide the most efficient protection for mailing sharps. In particular, a single plastic bag is not adequate as a sole means of providing the requisite leak-tightness; nor does a cardboard container used as the primary sharps container provide adequate puncture resistance. In addition, a cardboard container is not see-through and, therefore, does not allow for easy identification of a full container.

Accordingly, the need exists to provide an improved packaging system for handling, storing and transporting contaminated sharp medical waste which virtually eliminates the risk of human contact with sharps from the time they are deposited into a primary sharps container until their ultimate disposal.

SUMMARY OF THE INVENTION

In accordance with a preferred embodiment of the invention there is provided a mailer for packaging and shipping sharp medical waste comprising an outer shipping container, a water-tight secondary containment system enclosed within the outer shipping container, a leak-resistant, puncture-resistant primary container packaged within the secondary containment system, and an absorbent material within a water-tight barrier inside the outer shipping container.

More specifically, the present invention may comprise a disposable container for storing and shipping sharp medical waste. The container includes an outer shipping container having a closed bottom and an openable and closeable top. A secondary container thereof has a box having a closed bottom and an openable and closeable top and a plastic water-tight bag which has an open top and is receivable in the shipping container. The secondary container is of the same general shape as, but slightly smaller in dimensions than the exterior shipping container. Consequently, the secondary container is receivable in the plastic bag and capable of being securely enclosed within the outer container. The container also includes at least one puncture-resistant primary container having an open top for receiving articles and a closure for providing a leak resistant seal on the open top, the primary container being receivable in and capable of being securely enclosed within the secondary container. Consequently, breakage of the primary container is prevented during ordinary processing. An absorbent material is preferably contained in the disposable container, the material being capable of absorbing and retaining at least three times liquid allowed within the primary container.

Viewing the invention somewhat differently, it comprises a three-part packaging system in which a primary container may have a total liquid content volume of no more than 50 milliliters and be capable of remaining intact when exposed to temperatures between 0° and 120° F., a water-tight secondary containment system is designed to hold the primary container and prevent breakage of the primary container, and an outer shipping container securely holds the secondary containment system and prevents breakage of the primary container. The outer shipping container is preferably constructed from a 200-pound grade corrugated fiberboard or a material of equivalent strength, the overall packaging system having a total weight of no more than 35 pounds when the primary container is filled.

It is therefore an object of the present invention to provide a packaging system for safely transporting sharps through the postal system to an ultimate disposal location.

It is another object of the present invention to provide a packaging system for handling, storing and mailing sharps which retains its integrity when exposed to temperature and climate changes or rough handling associated with transport.

It is another object of the present invention to provide a packaging system which is completely leak-proof.

It is still another object of the present invention to provide a packaging system which is environmentally responsible and can, therefore, be almost completely destroyed through incineration to eliminate landfill waste.

It is still another object of the present invention to provide a packaging system in which the primary sharps container is of a size and configuration that provides for easy insertion of sharp objects, yet inhibits removal of the sharp objects, is puncture resistant and crack- and shatter-proof, and allows easy identification of a filled container.

These and other objects will become more apparent from the detailed description to follow.

BRIEF DESCRIPTION OF THE DRAWINGS

There follows a detailed description of the preferred embodiments of the present invention which are to be taken together with the accompanying drawings, wherein:

FIG. 2 is a perspective view of a primary container used in the mailer of the present invention;

FIG. 2A is a perspective view of another embodiment of the primary container;

DETAILED DESCRIPTION OF THE PREFERRED EMBODIMENTS

Referring now to the figures, like elements are represented by like numerals throughout the several views.

Figure 1:
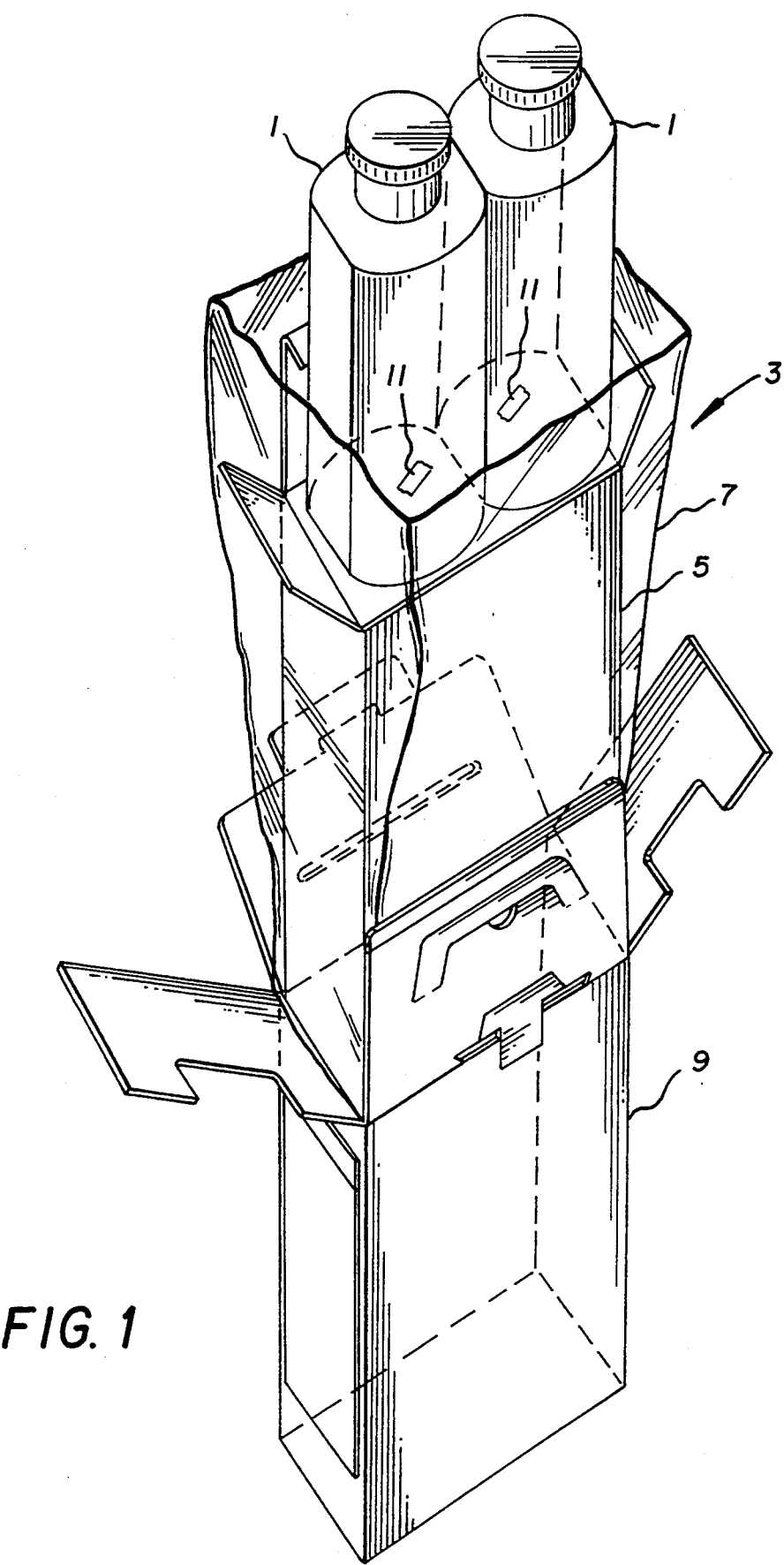
FIG. 1 is a perspective view of the various parts which comprise a mailer in accordance with the present invention.

FIG. 1 shows in a perspective view the various parts which comprise the mailer of the present invention prior to assembly but oriented as they are to be assembled. In general, at least one primary container 1 filled with sharps is placed in a secondary containment system 3. The secondary containment system 3 may, as shown, consist of more than one component, such as a fiberboard box 5 and a plastic liner 7, but will not consist of a plastic bag by itself. The secondary containment system 3 may be sized to hold more than one primary container 1, as shown; however, the secondary containment system 3 should be sized and constructed so as to completely enclose the primary container(s) 1 and prevent movement of the primary container(s) 1 when inserted therein. An absorbent material 11 is also enclosed within a water-tight barrier. As shown, the absorbent material 11 is located in the interior of the primary container(s) 1; however, it may also be placed between the secondary containment system 3 and the primary container(s) 1. The secondary containment system 3 is enclosed within an outer shipping container 9.

The primary container 1 may manufactured in various sizes. However, the container 1 should not be so large that it will be overly heavy in weight when filled. A smaller construction has the advantage of allowing the primary container 1 to be placed on a nearby counter or mounted on a wall in a laboratory or doctor's office for easy access. In addition, the amount of liquid allowed within any container 1 should not exceed 50 milliliters, to reduce the amount of potential leakage if the container 1 is broken. Preferably, a fill line 29 is also provided on the container 1 to indicate when it is at full capacity. In this regard, it is also desirable that a translucent material be used to manufacture the container thereby allowing for easy identification of the point at which the container is full. The container may also be an appropriate color which is indicative of the contents. Red, for example, is typically used to indicate a biohazardous material, while yellow is used to indicate chemotherapy waste. Alternatively, the container may be provided with the international biohazard symbol.

The primary container 1 is puncture resistant and capable of being securely sealed such that it is also leak-resistant. The container 1 will be subjected to various changes in climate during transport from an office or laboratory environment to a final disposal location. The primary container is, therefore, constructed of a material which maintains its integrity when exposed to temperatures between 0° and 120° F.; such suitable rigid materials include polypropylene, polycarbonate and high density polyethylene. Polycarbonate is the most preferred material of construction because it may be precisely extruded in various wall thicknesses, is hard and puncture resistant and is essentially clear. A suitable polycarbonate used in constructing the primary container 1 is LEXAN 154 which has been formulated to provide high heat and high impact resistance. A major drawback of polycarbonate, however, is that it cannot be used to manufacture larger containers due to cost considerations. High density polyethylene containers are typically manufactured by injection or, more preferably, blow molding. Containers made from this material are opaque, but not clear. Like polycarbonate, high density polyethylene is also hard and, therefore, puncture resistant. A suitable high density polyethylene is NHD 5604, which is available from Quantum Chemical Corporation. Polypropylene is least preferred because it tends to shatter at very low temperatures. In a preferred embodiment, the primary container is manufactured in a 3 quart size using polycarbonate, and manufactured in 2, 3½ and 6 gallon sizes using high density polyethylene.

FIG. 2 shows the preferred shape of the primary container 1 for the 3 quart size. Preferably, the primary container 1 comprises a bottle having a base portion 13 with four sides 19, 21, 23, 25, an open neck portion 15 and a top closure means 17. One set of opposed sides 19, 21 are preferably flat and rectangular in shape for conforming to the sides of a box. The other set of opposed sides 23, 25 are slightly rounded and of a size which enables the base portion 13 to be easily grasped and held by a human hand. The top closure means 17 may be any type of cap which provides a leak-proof seal. However, it is preferably a screw-type cap which can be easily opened and closed while still providing a leak-proof seal. A rubber gasket may also be inserted in the cap to compensate for an inexact fit between the cap and top opening which may occur during manufacture.

FIG. 2A shows a primary container similar to that of FIG. 2, but slightly different in shape and enlarged to hold 2 gallons. Similar to the 3 quart container, the 2 gallon container has one set of opposed sides 19', 21' which are flat and rectangular in shape for conforming to the sides of a box. However, the sides 19', 21' of the 2 gallon container are somewhat more elongated than the sides 19, 21 of the 3 quart container. Like the 3 quart container, the other set of opposed sides 23', 25' are slightly rounded. An open neck 15' and top closure means 17' are also provided. Generally, the 2 gallon container is manufactured from high density polyethylene and, consequently, opaque, while the 3 quart container is manufactured from polycarbonate which is clear.

Figure 3:
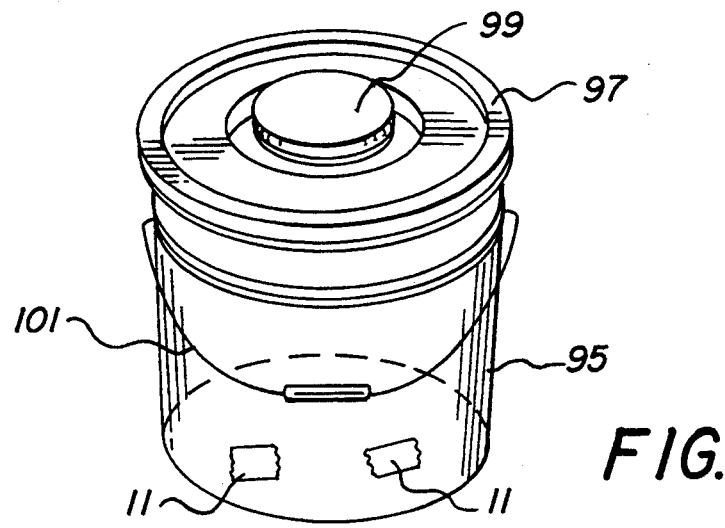
FIG. 3 is a perspective view of another embodiment of the primary container.

FIG. 3 shows the most advantageous configuration for a larger-sized primary container 1, on the order of 3½ gallons or more. Typically, the container is manufactured as two components comprising a pail 95 and a leak-proof lid 97. The lid 97 is provided with a central opening onto which leak-proof closure means 99, such as a screw-type cap, is affixed. A handle 101 may also be attached to the sides of the pail 95. Suitable primary containers in various sizes are commercially available from Blanke Plastic Company.

The absorbent material 11, shown at the bottom 31 of the base portion 13, is relatively lightweight so as not to add to the weight of the primary container 1 or mailer. Alternatively, the absorbent material may be disposed between the primary container 1 and the secondary containment system 3. The absorbent material 11 is preferably capable of absorbing and retaining at least three times the total liquid allowed within the primary container, or about 150 milliliters. One particularly effective absorbent material 11 is sodium polyacrylate. A small quantity of sodium polyacrylate is capable of absorbing and immobilizing a relatively large quantity of an aqueous solution by forming a gel-like material when it reacts therewith. Generally, sodium polyacrylate is contained within an envelope comprising a material which is degradable in the liquid which is to be absorbed. Suitable materials include a degradable starch paper which is partially coated with polyvinyl acetate. The polyvinyl acetate coating enables the envelope to be heat sealed. As shown in FIGS. 2 and 3, the requisite number of envelopes containing the absorbent material 11 may vary depending on the size of the primary container 1.

Other suitable absorbent materials include natural cellulosic, non-natural cellulosic or other similar materials which are biodegradable and combustible. However, to achieve the same absorbency provided by sodium polyacrylate it is necessary to use a larger quantity of these materials. Larger quantities, while undesirable in that they expend additional space, do have the advantage of providing a cushioning effect to prevent container breakage.

Figure 4:
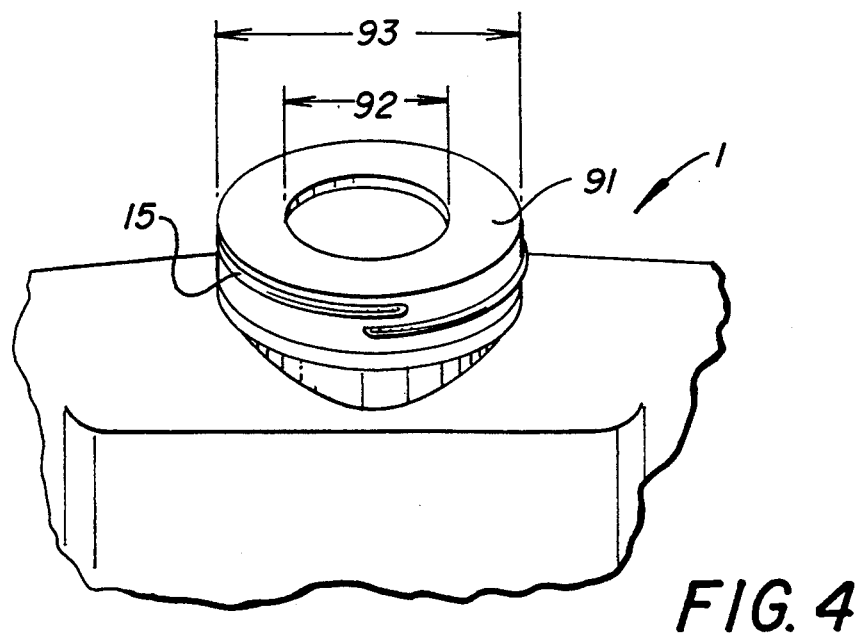
FIG. 4 is a perspective view of a preferred embodiment of the neck portion of the primary container.

FIG. 4 shows a preferred embodiment of the primary container 1 in which the neck portion 15 has a narrowed section 91 at the opening of the container 1 to prevent, or at least discourage, the insertion of a human hand and reduce the likelihood of sharps falling out of the primary container 1 if it is dropped or otherwise inverted. Typically, the exterior dimension of the neck portion 15 is not reduced in size because a larger closure means 17 is easier to handle. The outer diameter 93 of the neck portion 15 will generally range from about 3 to 5 inches, while the inner diameter 92 of the narrowed section 91 will range from approximately 1 to 2½ inches in diameter.

Figure 5:
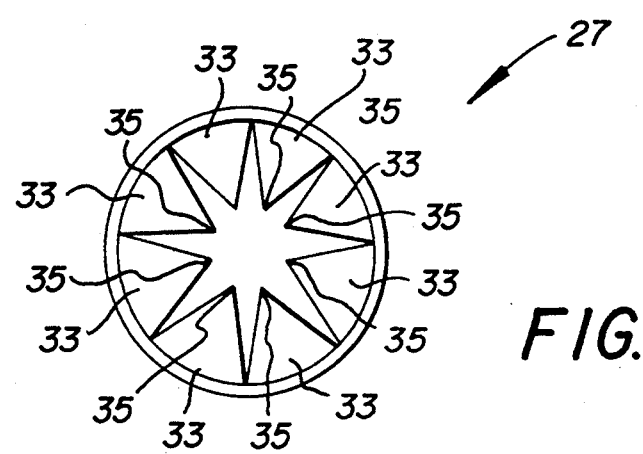
FIG. 5 is a top view of another embodiment of the neck portion of the primary container.

In an alternative embodiment, a funnel 27, may be disposed in the neck portion 15 to permit insertion of sharps into the base portion 13, but inhibit the sharps from falling out of the primary container 1. FIG. 5 shows a top view of the funnel 27 which comprises a plurality of adjacent pyramidal shaped panels 33. The panels are constructed of a flexible material, such as a plastic. The apexes 35 of the panels extend inwardly toward a central longitudinal axis of the primary container 1 and terminate proximate the center of the neck portion 15. The panels 33 are also biased downward toward the bottom 31 of the primary container 1 (see FIG. 2), so that passage of sharps into the container 1 is permitted while passage of sharps out of the container 1 is inhibited.

After the base portion 13 is filled, the top closure means 17 is secured and the primary container 1 is placed in a secondary containment system 3. The secondary containment system 3 is water-tight and supports the primary container 1 to prevent breakage during ordinary processing within the mail system. The secondary containment system may hold one or more primary containers, but should fully enclose all containers held therein. The secondary containment system 3 should, therefore, be of a size and shape which conforms to the shape of the primary container(s) 1.

Figure 6:
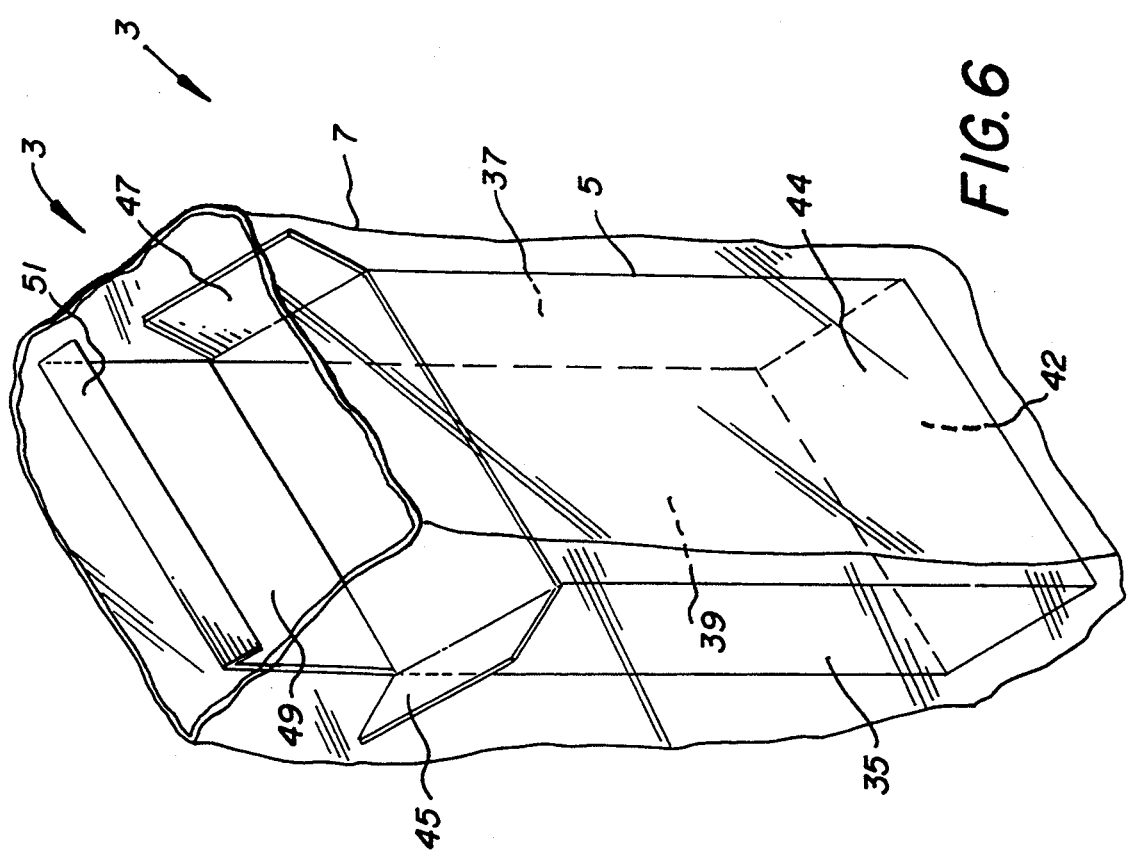
FIG. 6 is a perspective view of a preferred form of the secondary containment system comprising a corrugated fiberboard box and a plastic bag.

FIG. 6 shows a perspective view of a preferred secondary containment system 3 which comprises a corrugated fiberboard box 5 and a plastic bag 7, which essentially serves as a liner for the outer shipping container 9. The plastic bag 7 is used to provide the requisite water-tight seal and, accordingly, the box 5 is placed within the plastic bag 7. The bag may be closed with a twist tie or similar closure means. The plastic bag preferably has a thickness of at least 3 mils.

Figure 7:
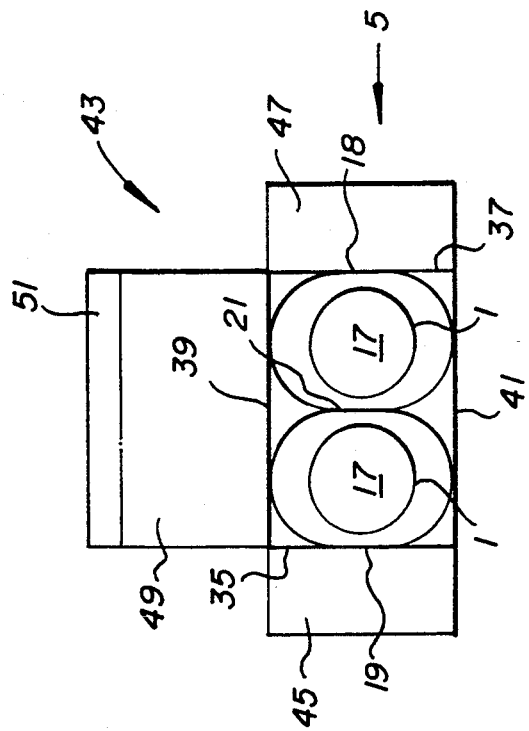
FIG. 7 is a top view of the box of FIG. 6 but reduced in size and shown receiving two primary containers.

The box 5 is of a generally rectangular construction, having a closed bottom 42, four side panels 35, 37, 39, 41 and an openable and closeable top 43. The box 5 is typically constructed of fiberboard. FIG. 7 shows a top view of the box 5 of the secondary containment system 3, sized to receive two primary containers 1. Typically, in this configuration, a primary container 1 is placed inside the box 5 such that one flat side panel 19 is adjacent a side wall 35, 37 of the box 5 and the other flat side panel 21 is adjacent the other primary container 1. Alternatively, the box 5 and/or primary containers 1 may have dimensions such that the primary containers are positioned with side panels 19 adjacent side walls 39, 41. On the other hand, where a larger-sized primary container, such as the one shown in the FIG. 3 embodiment, is utilized, the box 5 is typically sized to hold only a single primary container 1.

The top 43 of the box 5 is comprised of two side flaps 45, 47 and a top flap 49 which has a locking extension 51 which is inserted between the primary container(s) 1 and the opposed panel 41 to ensure that the box 5 remains sealed upon closure. The side flaps 45, 47 and the side panel 41 overlap with the top flap 49 upon closure, thereby reducing the open spaces through which the contents of the primary container 1 could potentially leak.

Alternative embodiments for the secondary containment system 3 include a plastic, curtain-coated fiberboard box or a container having a similar construction to that of the primary container 1. These embodiments provide the requisite water-tightness, yet are less desirable because they tend to be more costly than the combined fiberboard box/plastic bag system.

After the primary container 1 is sealed in the secondary containment system 3, it is placed in an outer shipping container 9. The outer shipping container 9 is preferably constructed of a 275-pound grade corrugated fiberboard, though 200-pound grade corrugated fiberboard or a similar material of equivalent strength is adequate to withstand the testing requirements imposed by the federal rules and regulations pertaining to mailability of sharps containers. Suitable fiberboard boxes for use in both the secondary containment system 3 and as an outer shipping container 9 are available from the Packaging Corporation of America. The secondary containment system 3 must fit securely within the outer shipping container 9 and, consequently, the outer shipping container 9 is typically of the same general shape, though slightly larger in dimension, than the secondary containment system 3. However, in selecting sizes, shapes and materials of construction for the outer shipping container 9, as well as the primary container 1 and secondary containment system 3, care should be taken to ensure that the final weight of the mailer, including sharps, will not exceed 35 pounds. In addition, the materials of construction should lend themselves to almost complete destruction through incineration, thereby minimizing the amount of landfill waste.

Figure 9:
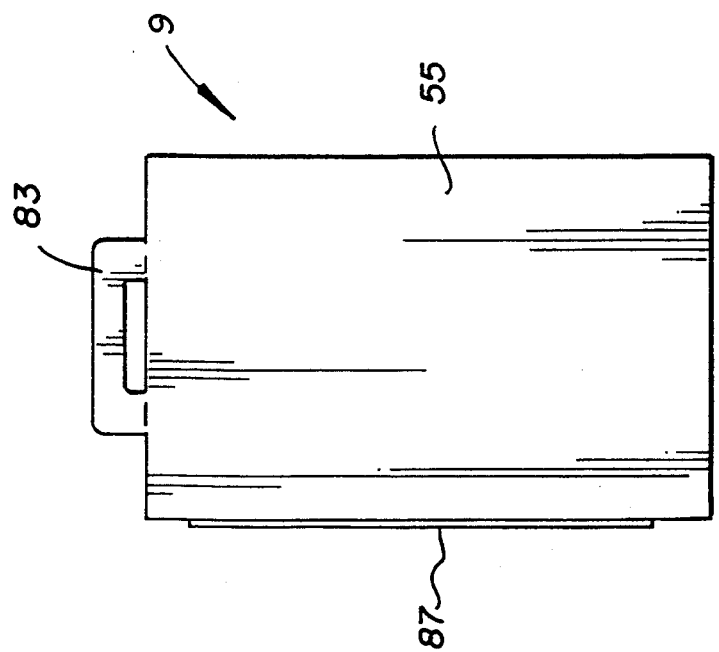
FIG. 9 is a front elevational view of a sealed mailer prepared for shipping.
Figure 8:
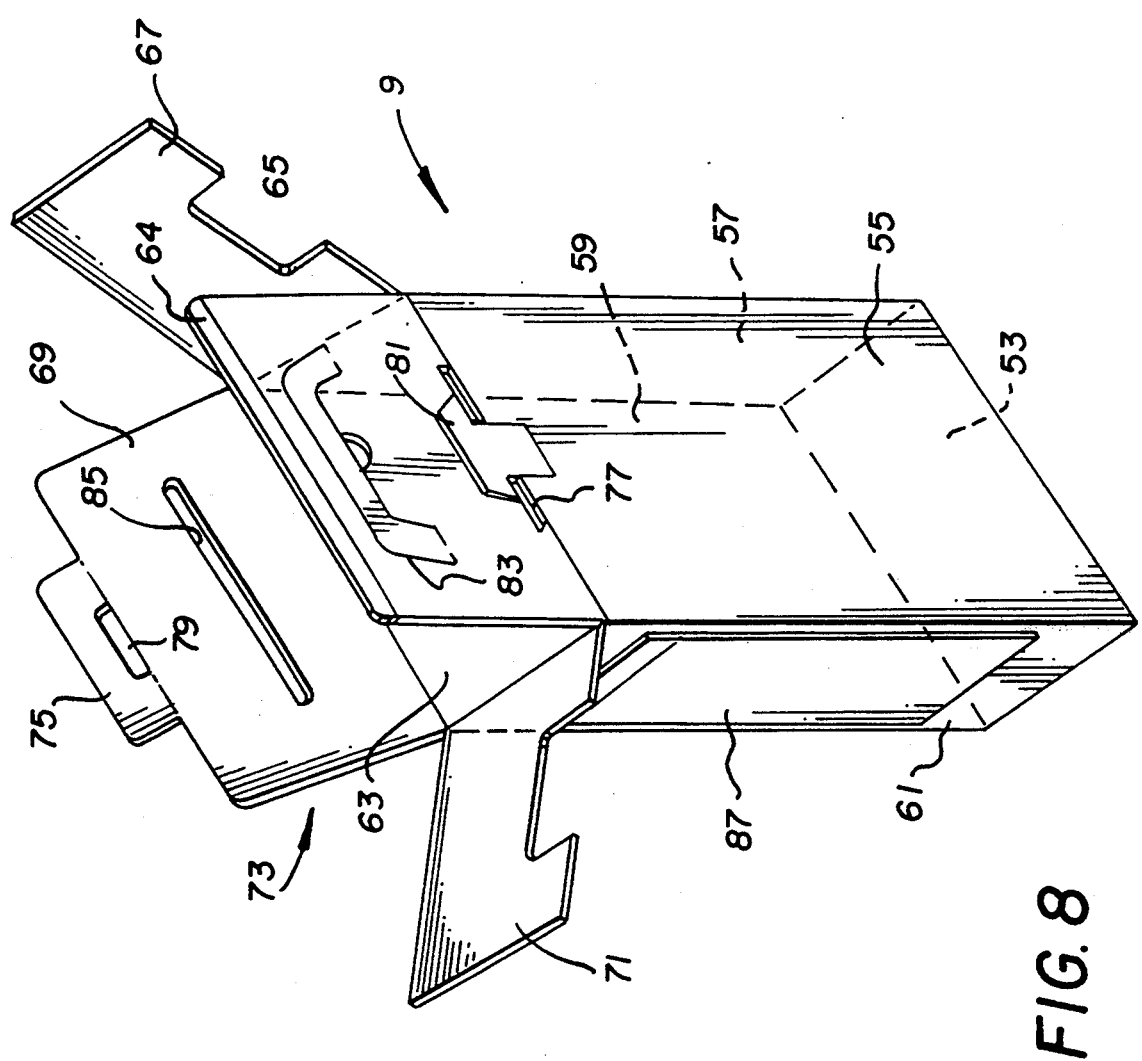
FIG. 8 is a perspective view of a preferred form of an outer shipping container.

FIG. 8 shows a preferred embodiment of the outer shipping container 9, comprising a closed rectangular bottom portion 53 and four rectangular side panels 55, 57, 59, 61 which define an open top 63. A top closure 73 is provided for sealing the outer shipping container 9. Preferably, the top closure 73 comprises four top panels 65, 67, 69, 71 hingedly secured to the side panels 55, 57, 59, 61, respectively. Each of the top panels 65, 67, 69, 71 is adapted to overlie the open top 63. Generally, after placing the secondary containment system 3, having the primary container 1 sealed therein, inside the outer shipping container 9, the outer shipping container is then sealed by first folding down top closure panels 67, 71, followed by folding down top closure panel 65. Top closure panel 65 further includes a locking extension 64 which is received between the opposing side panel 59 and the secondary containment system 3. Finally, top closure panel 69 is folded down and a locking extension 75 is inserted into a slot 77 in top closure panel 65 near the edge at which it intersects side panel 55. Locking extension 75 also includes an open slot 79 for receiving locking extension 81 which is attached to an upper edge of the opposed side panel 55. Top panel 65 further includes a handle portion 83 attached thereto which is inserted through a slot 85 in top closure panel 69. As shown in FIG. 9, the handle provides a simple means of carrying the mailer after it is sealed and ready for shipping, and also further reduces the risk of a person carrying the mailer contacting a sharp, in the unlikely event that it punctures through to the outside of the mailer.

The mailer also advantageously includes a sealable exterior side pocket 87 in which a shipping record may be enclosed. Preferably, the side pocket 87 is constructed of a transparent material, such as plastic, so that the contents listing, destination facility and other relevant information may be ascertained without the need to open the pocket 87.

Although the invention has been described in considerable detail with respect to preferred embodiments thereof, variations and modifications will be apparent to those skilled in the art without departing from the spirit and scope of the invention as set forth in the claims.

I claim:

1. A mailer for packaging and shipping sharp medical waste comprising;

an outer shipping container;

a water-tight secondary containment system enclosed within the outer shipping container;

a leak resistant, puncture-resistant primary container packaged within the secondary containment system, said primary container having an interior cavity for receiving a plurality of sharps and retaining said sharps loosely therein, and a closable opening for insertion of a plurality of sharps loosely therethrough into said interior cavity; and an absorbent material within a water-tight barrier inside the outer shipping container, said absorbent material comprising sodium polyacrylate in a degradable packaging, said absorbent material being capable of absorbing and retaining at least three times the total liquid capacity of the primary container.

2. The mailer according to claim 1 wherein the secondary containment system comprises a fiberboard box having a closed bottom, four side panels and an openable and closeable top.

3. The mailer according to claim 2 wherein the secondary containment system comprises a 200-pound grade corrugated fiberboard box.

4. The mailer according to claim 2 wherein the secondary containment system further comprises a plastic bag.

5. The mailer according to claim 4 wherein the box is enclosed in the plastic bag.

6. The mailer according to claim 4 wherein the absorbent material is contained between the primary container and the plastic bag.

7. The mailer according to claim 1 further comprising a second primary container.

8. The mailer according to claim 1 wherein the absorbent material is contained in the primary container.

9. The mailer according to claim 1 wherein the primary container comprises a bottle or a pail having an open neck portion and a screw-type top closure means for sealing said open neck portion.

10. The mailer according to claim 9 wherein the primary container further comprises a narrowed section in the neck portion, whereby passage of articles into the primary container is permitted and passage of articles out of the primary container is inhibited.

11. The mailer according to claim 9 wherein the primary container further comprises a funnel disposed inside the neck portion, whereby passage of articles into the primary container is permitted and passage of articles out of the primary container is inhibited.

12. The mailer according to claim 1 wherein the primary container is constructed of a material which maintains its integrity when exposed to temperatures of 0 to 120 degrees Fahrenheit.

13. The mailer according to claim 12 wherein the material used for manufacture of the primary container is selected from the group consisting of high density polyethylene and polycarbonate.

14. The mailer according to claim 1 wherein the primary container has a liquid capacity of 50 milliliters or less.

15. The mailer according to claim 1 wherein the outer container comprises:
   a closed rectangular bottom portion;
   four rectangular side panels with upper edges defining an open top; and
   a top closure comprising four top panels hingedly secured at lower edges to the upper edges of respective side panels, each of the top panels being adapted to overlie the open top.

16. The mailer according to claim 15 further comprising a handle portion.

17. A disposable container for storing and shipping sharp medical waste comprising:
   an outer container comprising a box having a closed bottom and an openable and closeable top;
   a secondary container comprising a box and a plastic water-tight bag, said plastic water-tight bag having an open top, said box having a closed bottom and an openable and closeable top and being of the same general shape as, but slightly smaller in dimension than, the outer container, whereby the secondary container is receivable in the outer container and capable of being securely enclosed therein;
   at least one puncture-resistant primary container having an open top for receiving articles and closure means for providing a leak resistant seal on the open top, the at least one primary container being receivable in and capable of being securely enclosed within the secondary container, whereby breakage of the primary container is prevented during ordinary handling; and
   an absorbent material capable of absorbing and retaining at least three times the liquid capacity of the primary container.

18. The disposable container according to claim 17 wherein the plastic bag has a thickness of at least 3 mils.

19. The disposable container according to claim 17 wherein the secondary container is constructed from 200-pound grade corrugated fiberboard.

20. The disposable container according to claim 17 wherein the outer container is constructed from 275-pound grade corrugated fiberboard.

21. A disposable container according to claim 17 further comprising a side pocket on the outer container for holding a shipping record.

22. A disposable container according to claim 17 wherein the secondary containment systems comprises a fiberboard box having a closed bottom, four side panels and an openable and closeable top.

23. A disposable container according to claim 17 wherein the primary container comprises a bottle or a pail having an open neck portion, a narrow section within said open neck portion and a screw-type top closure means for sealing said open neck portion.

24. A disposable container according to claim 23 wherein size of the primary container ranges from 3 quarts to 6 gallons.

25. A mailer for packaging and shipping medical waste comprising:
   an outer shipping container;
   a water-tight secondary containment system enclosed within the outer shipping container, the secondary containment system comprising a fiberboard box enclosed within a plastic bag;
   a leak-resistant, puncture-resistant primary container packaged within the secondary containment system; and
   an absorbent material within a water-tight barrier inside the outer shipping container.

26. The mailer according to claim 25 wherein the fiberboard box comprises a 200-pound grade corrugated fiberboard box.

27. The mailer according to claim 25 further comprising at least two primary containers.

28. The mailer according to claim 25 wherein the primary container includes an interior cavity for receiving a plurality of sharps and retaining said sharps loosely therein, and a closable opening for insertion of a plurality of sharps loosely therethrough into said interior cavity.

29. The mailer according to claim 25 wherein the absorbent material is capable of absorbing and retaining at least three times the total liquid allowed within the primary container.

30. The mailer according to claim 29 wherein the absorbent material is sodium polyacrylate packaged in an envelope, the envelope comprising a material which is degradable in a liquid contained in the primary container.

31. The mailer according to claim 25 wherein the absorbent material is contained in the primary container or the secondary containment system.

* * * * *